United States Patent
Wolford

(10) Patent No.: US 6,875,217 B2
(45) Date of Patent: Apr. 5, 2005

(54) ORTHOPAEDIC REAMER ASSEMBLY

(75) Inventor: Todd Wolford, Goshen, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 0 days.

(21) Appl. No.: 10/338,479

(22) Filed: Jan. 8, 2003

(65) Prior Publication Data

US 2004/0133210 A1 Jul. 8, 2004

(51) Int. Cl.⁷ .............................................. A61B 17/00
(52) U.S. Cl. ........................................................ 606/81
(58) Field of Search .............................. 606/53, 80, 81, 606/79, 83, 84, 86, 96, 99; 403/325, 347, 359.3, 322.1

(56) References Cited

U.S. PATENT DOCUMENTS

| | | | |
|---|---|---|---|
| 4,662,891 A | * 5/1987 | Noiles | 623/22.31 |
| 5,100,267 A | * 3/1992 | Salyer | 407/54 |
| 5,171,313 A | 12/1992 | Salyer | 606/86 |
| 5,462,548 A | 10/1995 | Pappas et al. | 606/80 |
| 5,501,686 A | 3/1996 | Salyer | 606/79 |
| 5,658,290 A | 8/1997 | Lechot | 606/80 |
| 5,817,096 A | 10/1998 | Salyer | 606/81 |
| 6,168,600 B1 | 1/2001 | Grace et al. | 606/81 |
| 6,250,858 B1 | 6/2001 | Salyer | 408/239 |
| 6,283,972 B1 | 9/2001 | Riley | 606/81 |

* cited by examiner

Primary Examiner—Kevin Shaver
Assistant Examiner—Anu Ramana
(74) Attorney, Agent, or Firm—Taylor & Aust, P.C.

(57) ABSTRACT

An orthopaedic reamer assembly includes a reamer with a generally hemispherical shell having a concave side and at least one attachment feature associated with the concave side. A driver is attachable to the reamer. The driver includes a shaft with a reamer end. The reamer end removably attaches to at least one attachment feature.

1 Claim, 4 Drawing Sheets

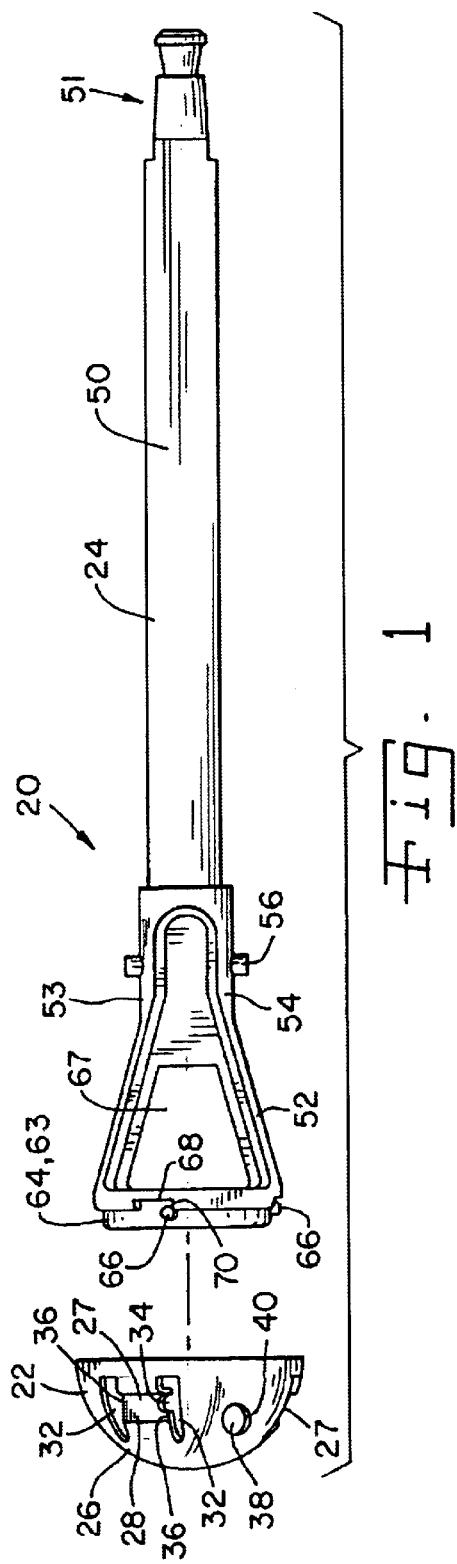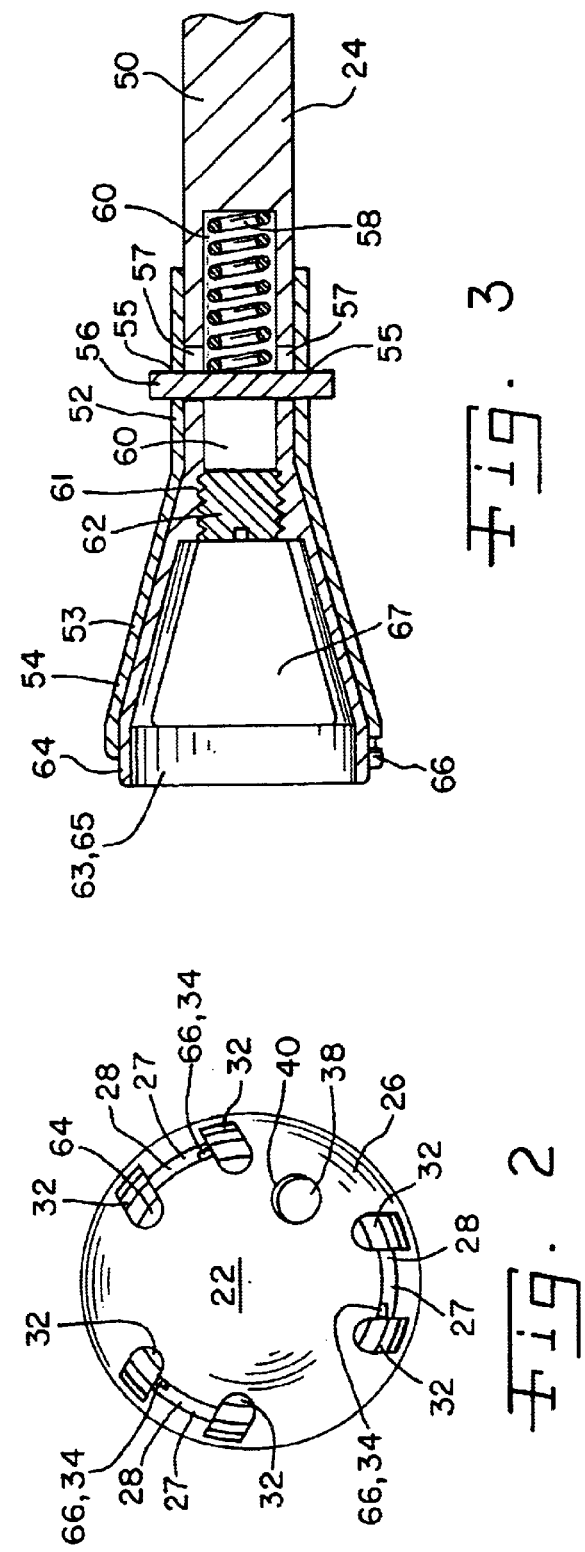

ORTHOPAEDIC REAMER ASSEMBLY

BACKGROUND OF THE INVENTION

1. Field of the Invention

The present invention relates to orthopaedic instruments, and, more particularly, to an apparatus and method of attaching an orthopaedic reamer to an orthopaedic driver.

2. Description of the Related Art

Orthopaedic reamers and drivers may be used to prepare the acetabulum for hip joint prosthesis. A rotary tool provides the motive force and is connected to the driver which is connected to the reamer. The drivers generally have a shaft and a reamer end. Reamers are generally hemispherical in shape and attach to the reamer end at the base of the hemisphere. The interior portion of the reamer is known as the debris cavity.

Connecting the driver reamer end to the reamer is known to include attachment of the driver to the base of the reamer. The reamer base can include various backing plates, crossbars and pins which the driver grips. In manufacturing such a reamer, the hemispherical shell can be deep drawn and then assembly of the reamer base to the backing plate, etc. is required. Therefore, this type of design requires multiple production steps including labor and cost intensive methods such as welding, grinding and polishing. Another disadvantage of known mounting methods includes the cost and time to manufacture the various backing plates, etc.

In use, the designs discussed above are problematic in that backing plates and the like mounted to the reamer base block the debris cavity. Such mounting techniques also have surfaces which do not have line of sight access, being blocked by either the hemispherical shell or a surface of the backing plate, thereby making the reamer difficult to clean and sterilize. Given the fact that these instruments are required to be sterile before use and are used in a sterile field (the operating room), every precaution must be exercised in cleaning the instruments, which makes a difficult cleaning procedure time intensive.

When the reamer is used to prepare the acetabulum for hip joint prosthesis, variation in the size of the acetabulum for the human population requires a range of sizes of acetabular reamers, a specific size of the acetabular reamer being determined by the hip joint size of the person undergoing hip joint prosthesis. The different sizes of acetabular reamers are generally specified by different radii of curvature, or diameters, of the hemispherical shell. Some of the known methods of mounting reamers to drivers, because of the attachment of the base of the reamer to the driver, and therefore a dependency on the reamer diameter, require modifications to the driver or different drivers for different size reamers. This increases the cost of a tool set that can accommodate a wide range of hip joint size.

What is needed in the art is apparatus and method of attaching a reamer to a driver that provides ease of manufacturing the reamer, minimizes or eliminates the debris cavity blockage, is suitable for easy and thorough cleaning and sterilization and in which a single driver can be used for a range of reamer sizes.

SUMMARY OF THE INVENTION

The present invention provides a reamer and driver wherein the driver attaches to the inside, or concave, surface of the reamer.

The invention comprises, in one form thereof, an orthopaedic reamer assembly including a reamer with a generally hemispherical shell having a concave side and at least one attachment feature associated with the concave side. A driver is attachable to the reamer. The driver includes a shaft with a reamer end. The reamer end is removably attached to at least one attachment feature.

An advantage of the present invention is an orthopaedic reamer assembly including a single piece reamer that is relatively easy and cost effective to manufacture.

Another advantage of the present invention is an orthopaedic reamer assembly that minimizes or eliminates the debris cavity blockage.

Yet another advantage of the present invention is an orthopaedic reamer assembly suitable for easy and thorough cleaning and sterilization.

A further advantage of the present invention is an orthopaedic reamer assembly wherein a single driver can be used for a range of reamer sizes.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is an exploded, side view of an embodiment of the orthopaedic reamer assembly of the present invention;

FIG. 2 is top view of the orthopaedic reamer assembly shown in FIG. 1;

FIG. 3 is a cross-sectional view of the reamer driver shown in FIG. 1;

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 4:
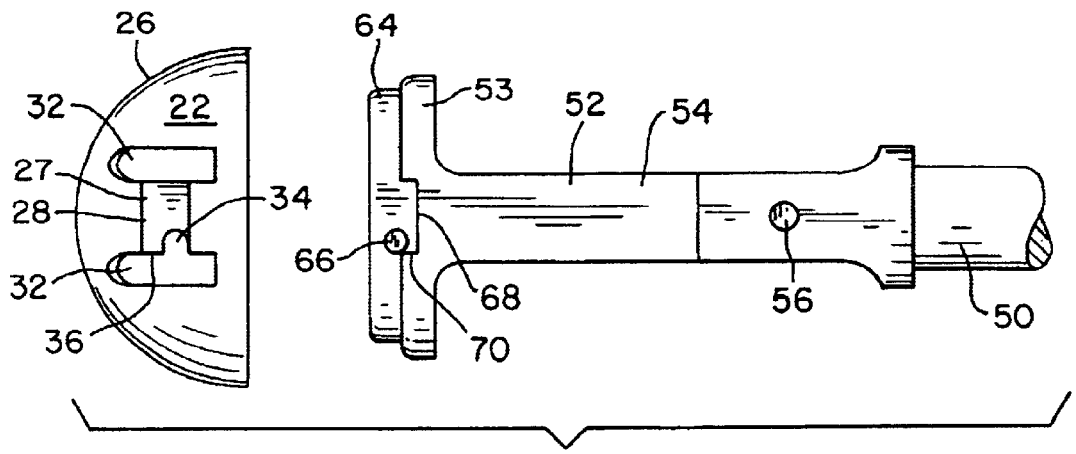
FIG. 4 is an exploded view of the driver reamer end and reamer of the present invention showing the releasable collar in a closed position.

Referring now to the drawings, and more particularly to FIGS. 1–3 and 9, there is shown an orthopaedic reamer assembly 20 which generally includes reamer 22 and driver 24.

Reamer 22 includes hemispherical shell 26 with at least one attachment feature 27 protruding on concave side 30

Figure 9:
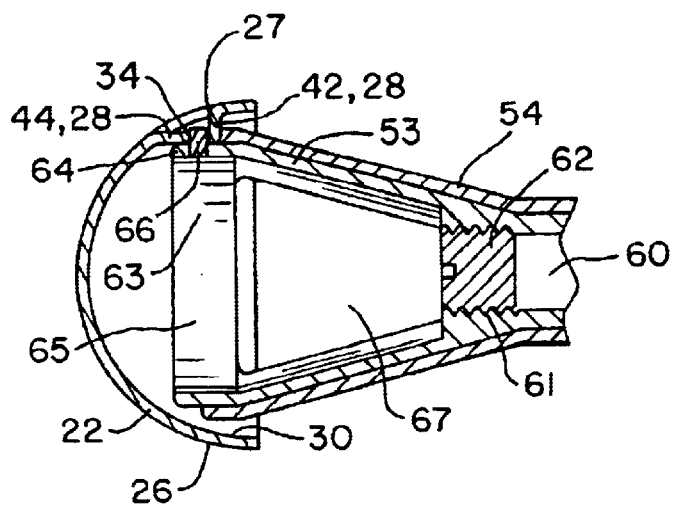
FIG. 9 is a cross-sectional view taken along section line 9—9, in FIG. 8.

(FIG. 9). In the embodiment shown in FIG. 2, hemispherical shell 26 has three attachment features 27. Attachment feature 27 includes indent 28 having at least one attachment slot 32 adjacent each indent 28 with at least one of attachment slots 32 including recess 34. At least one locating edge 36 is formed at the edge of indent 28. In the embodiment shown, indent 28 includes base portion 42 at approximately 90° to wall portion 44, as best seen in FIG. 9, although base portion 42 and wall portion 44 can have other relative angles. Attachment slots 32 and recesses 34 are apertures formed in hemispherical shell 26 and indents 28 are a portion of shell 26 formed inward toward concave side 30. Reamer 22 further includes a plurality of cutting apertures 38 having cuffing surface 40. In the embodiment shown, only a single cutting aperture 38 is depicted for sake of clarity. Reamer 22 typically has a plurality of cutting apertures 38 and surfaces 40 located to provide 180° cutting coverage during rotation of reamer 22. Cutting apertures 38 and surfaces 40 can take a variety of shapes, and additionally, other apertures (not shown) can be included in reamer 22.

Driver 24 includes shaft 50 connected to reamer end 52. Shaft 50 is a generally elongate cylindrical shape with connective features 51 opposite reamer end 52. Reamer end 52 includes releasable collar 53 with sleeve 54 fitted over boss 64. Biasing element 58 is mounted in cavity 60. Biasing element 58 is shown in FIG. 3 as a coil spring but can also be other spring types such as a leaf or spiral spring, or other biasing elements such as a compressible fluid filled container or a rubber or other resilient material elements. Release pin 56 is press fit into holes 55 in sleeve 54. Release pin 56 is conveyed through pin slots 57 and cavity 60 during the press fit operation wherein biasing element 58 biases release pin towards threaded element 62 thereby biasing sleeve 54 in a normally closed position as shown in FIG. 3. Threaded element 62 allows access to cavity 60 for assembly of biasing element 58 and release pin 56, and additionally, to seal cavity 60 from surgical debris (not shown) and other contamination (also not shown). Threaded element 62 threads into cavity threaded portion 61.

Sleeve 54 includes at least one groove 68 located proximate to at least one retaining pin 66 in boss 64. In the embodiment shown, there are three grooves 68 and three retaining pins 66 corresponding to three attachment features 27. Groove 68 is complimentary in shape to indent 28 of attachment feature 27.

Boss 64 includes ring 63 defining ring hole 65 therein. Boss 64 further includes open area 67.

Figure 5:
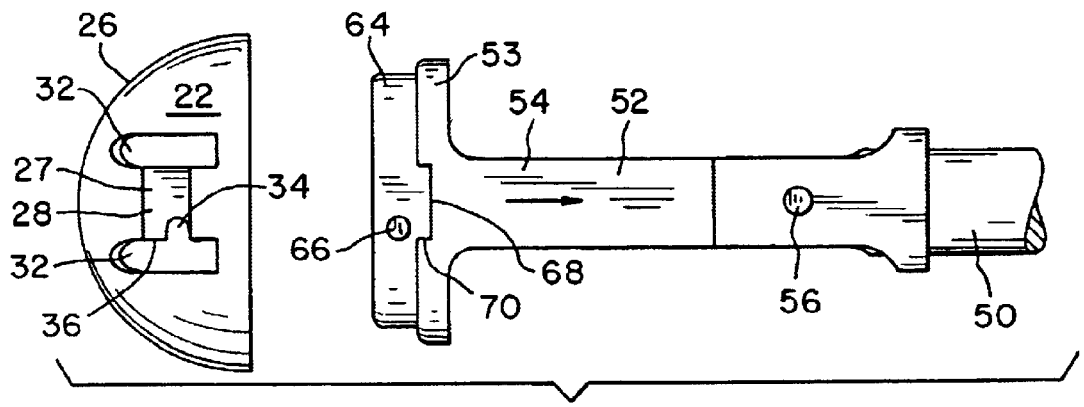
FIG. 5 is an exploded view showing the releasable collar in an open position.
Figure 6:
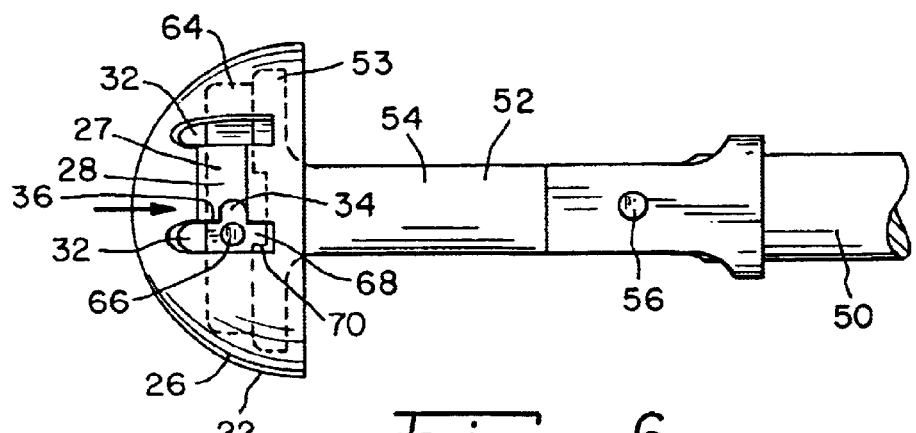
FIG. 6 is an assembled view showing the releasable collar in an open position.
Figure 7:
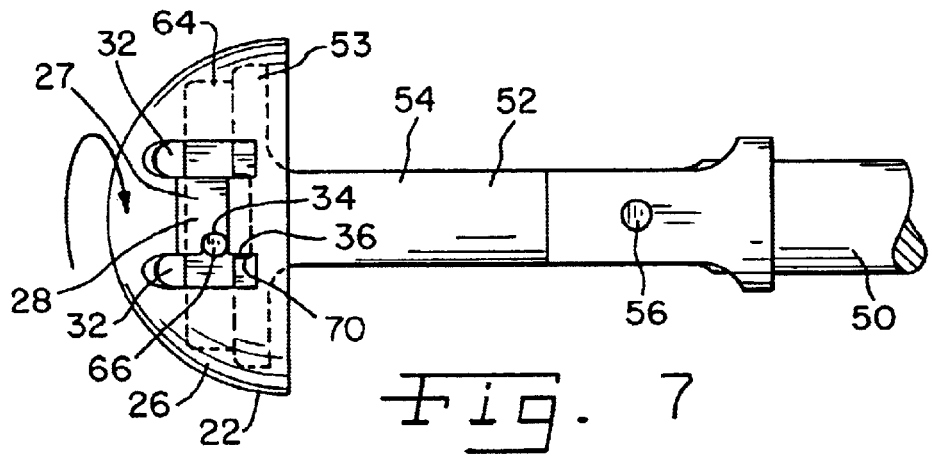
FIG. 7 is an assembled view showing the reamer positioned for locking but the releasable collar in an open position.
Figure 8:
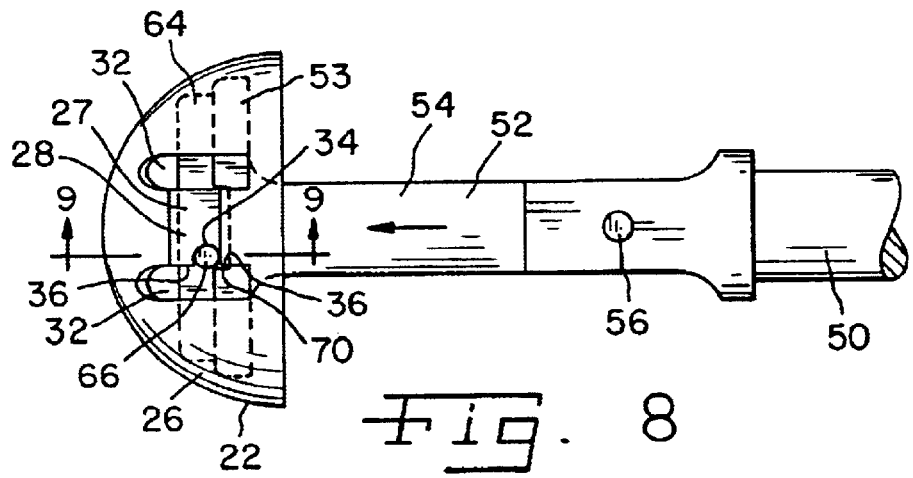
FIG. 8 is an assembled view showing the reamer in a locked position and the releasable collar in a closed position.

To attach reamer 22 with driver 24, reamer 22 is positioned proximate to driver 24 with attachment feature 27 approximately aligned with retaining pin 66 and groove 68 as shown in FIG. 4. Sleeve 54 is biased in an open position as shown in FIG. 5. Concave side 30 of reamer 22 is mounted onto reamer end 52 of driver 24 (FIG. 6) with sleeve 54 held in the open position. With sleeve 54 still held in the open position, reamer 22 is rotated slightly (FIG. 7) to engage retaining pin 66 in recess 34. Sleeve 54 is released to the closed position (FIG. 8) wherein groove end 70 constrains retaining pin 66 in recess 34 thereby locking reamer 22 to driver 24. If reamer 22 has multiple attachment features 27, all attachment features 27 are engaged concurrently by corresponding retaining pins 66 and grooves 68. Dismounting reamer 22 from driver 24 is simply the reverse aforementioned mounting procedure.

Figure 10:
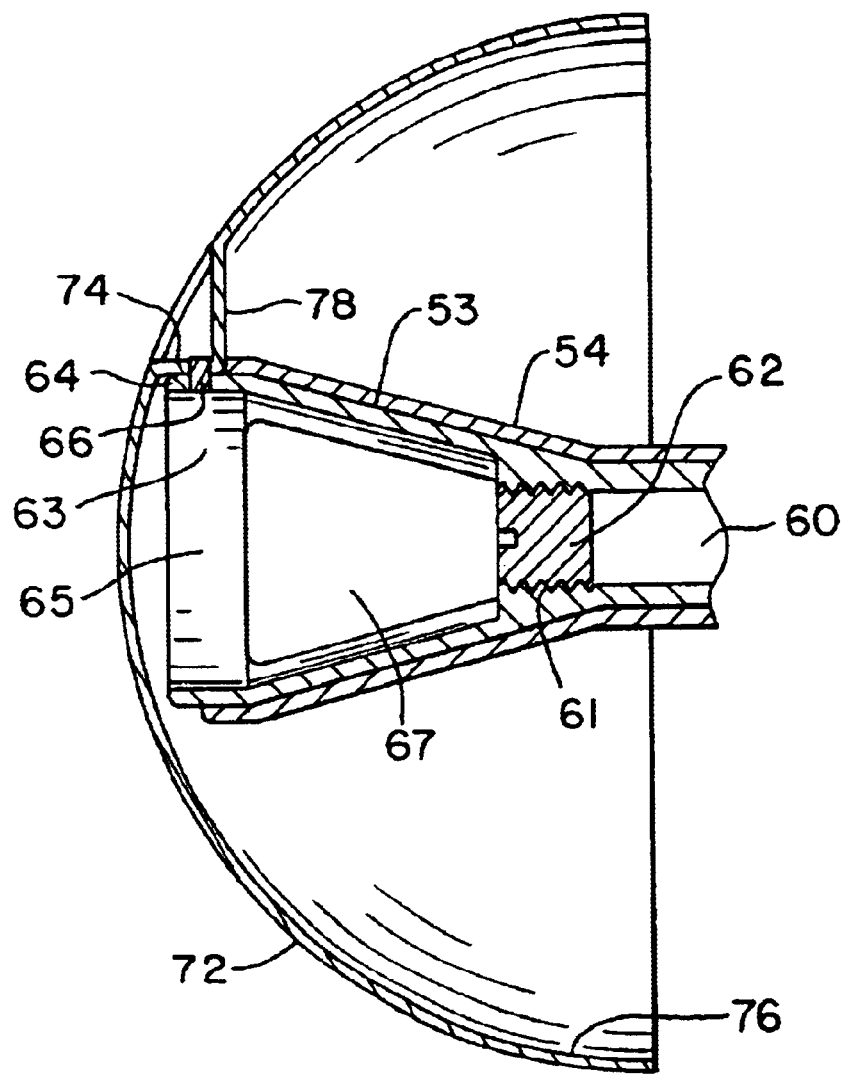
FIG. 10 is a cross-sectional view of another embodiment of an assembled driver reamer end and reamer, showing a larger diameter reamer mounted on the same driver as FIG. 9.

FIG. 9 shows orthopaedic reamer assembly 20 with reamer 22 mounted on driver 24 and with reamer 22 of a relatively small size. FIG. 10 depicts the same driver 24 of FIG. 9, but with a relatively large reamer 72 mounted on driver 24. Attachment feature 74 on concave side 76 of large reamer 72 are basically similar to attachment features 27 with the primary difference being an extra length in base portion 78. Driver 24 fits farther towards the apex of large reamer 74 but otherwise attaches similar to reamer 22.

Surgical debris (not shown) can exit orthopaedic reamer assembly 20 between boss 64 and concave side 30 or through ring 63 and open area 67. All exposed surfaces in both reamer 22 and driver 24 have line of sight access facilitating easy and thorough cleaning and sterilization.

Single piece reamer 22 is relatively easy and cost effective to manufacture. Driver 24 facilitates quick and convenient attachment of reamer 22. A single driver 24 can be used for a range of reamer sizes. The design of both reamer 22 and driver 24 minimizes or eliminates the debris cavity blockage during surgical procedure and cleaning and sterilization.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic driver, comprising:

a shaft with a reamer end; and a releasable collar disposed on said reamer end, said releasable collar including a boss having at least one retaining pin; a sleeve fitted over said boss, said sleeve including at least one groove, each said groove proximate to a corresponding said retaining pin; a cavity in said reamer end; a biasing element in said cavity, said biasing element biasing said sleeve in a closed position respective to said boss; and a release pin in said reamer end, said release pin press fit into said sleeve, said release pin conveyed through said cavity, said biasing element biasing against said release pin.

* * * * *